United States Patent
Beller et al.

[11] Patent Number: 5,961,446
[45] Date of Patent: Oct. 5, 1999

[54] PATIENT TERMINAL FOR HOME HEALTH CARE SYSTEM

[75] Inventors: Alexander S Beller, Newtown Square; Joseph Colombo, Newtown; Adrien J Hribar, Langhorne; Ilene K Warner, Broomall; Frank Fabian, Kintnersville; Michael E Mocenter, Dresher, all of Pa.

[73] Assignee: Tevital Incorporated, Berwyn, Pa.

[21] Appl. No.: 08/691,507

[22] Filed: Aug. 2, 1996

Related U.S. Application Data

[60] Provisional application No. 60/004,882, Oct. 6, 1995.

[51] Int. Cl.⁶ .................................................. A61B 5/00
[52] U.S. Cl. ........................... 600/300; 600/301; 128/904
[58] Field of Search ................... 600/300, 301, 600/481, 483; 128/903, 904; 340/286.06, 286.07, 825.16, 825.37, 505, 506, 573; 348/14; 379/38, 67; 364/922, 922.4

[56] References Cited

U.S. PATENT DOCUMENTS

| | | | |
|---|---|---|---|
| 4,259,548 | 3/1981 | Fahey et al. | 179/5 R |
| 4,337,377 | 6/1982 | Van Riper et al. | 179/2 R |
| 4,803,625 | 2/1989 | Fu et al. . | |
| 4,837,719 | 6/1989 | McIntosh et al. | 364/569 |
| 4,838,275 | 6/1989 | Lee | 128/670 |
| 4,933,873 | 6/1990 | Kaufman et al. | 364/513.5 |
| 4,974,607 | 12/1990 | Miwa | 128/904 |
| 5,036,462 | 7/1991 | Kaufman et al. | 364/413.01 |
| 5,084,828 | 1/1992 | Kaufman et al. | 364/479 |
| 5,102,008 | 4/1992 | Kaufman et al. | 221/25 |
| 5,142,484 | 8/1992 | Kaufman et al. | 222/638 |
| 5,148,944 | 9/1992 | Kaufman et al. | 221/131 |
| 5,197,632 | 3/1993 | Kaufman et al. | 221/197 |
| 5,230,441 | 7/1993 | Kaufman et al. | 221/25 |
| 5,307,263 | 4/1994 | Brown | 364/413.09 |
| 5,329,459 | 7/1994 | Kaufman et al. | 364/479 |
| 5,335,816 | 8/1994 | Kaufman et al. | 221/13 |
| 5,339,821 | 8/1994 | Fujimoto . | |
| 5,357,427 | 10/1994 | Langen et al. | 364/413.02 |
| 5,390,238 | 2/1995 | Kirk et al. | 379/93 |
| 5,410,471 | 4/1995 | Alyfuku et al. | 364/413.02 |
| 5,441,047 | 8/1995 | David et al. | 128/670 |
| 5,442,728 | 8/1995 | Kaufman et al. | 395/2.79 |
| 5,454,722 | 10/1995 | Holland et al. . | |
| 5,495,961 | 3/1996 | Maestre | 368/10 |
| 5,553,609 | 9/1996 | Chen et al. | 128/630 |
| 5,612,869 | 3/1997 | Letzt et al. | 395/203 |

FOREIGN PATENT DOCUMENTS

| | | | |
|---|---|---|---|
| 2675288 | 4/1991 | France | G06F 15/42 |
| 2717332 | 3/1994 | France | H04L 12/00 |
| 456561 | 2/1992 | Japan | H04M 11/00 |
| 4306046 | 10/1992 | Japan | H04M 11/00 |
| 77560 | 1/1995 | Japan | H04M 11/00 |
| 9319667 | 10/1993 | WIPO | A61B 5/0408 |

*Primary Examiner*—Michael Peffley
*Assistant Examiner*—Bryan K. Yarnell
*Attorney, Agent, or Firm*—Elman & Associates

[57] ABSTRACT

A teleconferencing system uses video conferencing between a nurse station and a patient station to deliver medical care. The patient station is programmed to contain customized instructions concerning medications, procedures, or visitations that were placed there by the nurse. The customized audio, video and text information transforms the patient station into a highly personalized information source which can be reviewed by the patient when the unit is off line. Medical procedures and medications are also programmed into the patient station by the nurse to remind the patient of all scheduled events, including visitations. A record of medical compliance is stored in the patient station, which record is uploaded to the nurse station and compared to the original event schedule. In such manner, the patient station is an intelligent personal medical assistant, programmed by the nurse to provide customized reminders and information necessary for the efficient management of the patient's illness. The patient station is easy to use, including only four large buttons which are re-definable by notations on a video screen, and, for the convenience of the patient, the video camera at the patient station is remotely controlled by the nurse to obtain the desired view without requiring that the patient move.

10 Claims, 9 Drawing Sheets

```
┌─────────────────────────────────────┐
│ □   PATIENT MEDICAL RECORD          │
├─────────────────────────────────────┤
│ JONES, BOB                          │
│  GENERAL MEDICAL INFORMATION/HISTORY│
│  ─────────────────────────────────  │
│  ─────────────────────────────────  │
│  ─────────────────────────────────  │
│  RECORD OF VISITS/TREATMENTS        │
│  DATE OF VISIT ____________         │
│  SERVICE PERFORMED ____________     │
│  DATA COLLECTION BP____________     │
│                  HR____________     │
│                  TEMP____________   │
│  DATE OF VISIT ____________         │
│  SERVICE PERFORMED ____________     │
│  DATA COLLECTION BP                 │
│  ┌──────────────┐  ┌──────────────┐ │
│  │ SAVE RECORD  │  │ CLOSE WINDOW │ │
│  └──────────────┘  └──────────────┘ │
│  ┌──────────────┐  ┌──────────────────┐ │
│  │INITIALIZE VISIT│ │OPEN BILLING RECORD│ │
│  └──────────────┘  └──────────────────┘ │
└─────────────────────────────────────┘
          ↓
   ┌────────────────┐
   │ TERMINATE VISIT│
   └────────────────┘
```

FIG. 13

```
┌─────────────────────────┐
│ □      PATIENT LIST     │
├─────────────────────────┤
│    SELECT OR TYPE       │
│    PATIENT NAME         │
│    ┌──────────┐         │
│    │ JONES,BOB│         │
│    └──────────┘         │
│ ┌─────────────────────┐ │
│ │ DOE, JOHN           │ │
│ │ HALL, CARTER        │ │
│ │ JONES, BOB          │ │
│ │ JONES, JACK         │ │
│ │ PARKER, PETER       │ │
│ │ RICHARDS, REED      │ │
│ │ SMITH, SALLY        │ │
│ └─────────────────────┘ │
└─────────────────────────┘
```

```
┌─────────────────────────────────────────┐
│ □       PATIENT STATION DATA            │
├─────────────────────────────────────────┤
│  STATUS OF CONNECTION    │ CONNECTED │  │
│                                         │
│  BLOOD PRESSURE          │ 120/80    │  │
│                                         │
│  HEART RATE              │ 60        │  │
│                                         │
│  TEMPERATURE             │ 98.5      │  │
│                                         │
│  STETHOSCOPE             │ FILENAME  │  │
│                                         │
│  ONLY AFTER REVIEW       │ RECORD    │  │
│  BY A TRAINED MEDICAL    │STETHOSCOPE│  │
│  PROFESSIONAL                           │
└─────────────────────────────────────────┘
```

PATIENT TERMINAL FOR HOME HEALTH CARE SYSTEM

CROSS REFERENCE TO RELATED APPLICATIONS

This application claims priority from provisional application Ser. No: 60/004882, filed Oct. 6, 1995.

FIELD OF THE INVENTION

The present invention relates to telecommunications and medicine. In particular, the present invention relates to the use of video conferencing and teleconferencing to deliver medical care.

BACKGROUND OF THE INVENTION

In a video conference, two or more people are connected over a telephone line or other suitable two way communications channel, such as POTS, ISDN, CATV, cellular, satellite, radio or fiber optic link. Each participant sees and hears the other party, and in a teleconference generally, may additionally view commonly shared text, diagrams and photographs. Video conferencing equipment has been used for medical purposes, such as for doctor consultation and diagnosis, or routine monitoring by nurses. In addition, it is known to provide sensors to measure the patient's vital signs, such as temperature, pulse rate and blood pressure, and transfer the measurements across the telephone line from the patient station to the doctor or nurse. Other sensors, such as fetal monitors have been used to take measurements on a patient at home (or other remote site such as a hospital, school, clinic, factory, ship or the like), and to transfer the output over the telephone line to the medical office or other health provider locale.

Medical visits by a nurse (or other health care professional such as a therapist, EMT or physician) via video conference or teleconference provides an alternative to office visits by the patient, or to home visits by the nurse. Teleconference visits may be used to check up on patient recovery progress, verify medication compliance, to illustrate to a patient during the electronic visit as to how to perform home care, and the like. A teleconference visit is a convenience to the patient, especially for those patients who would have difficulty traveling to the doctor's office or hospital. A video conference visit, connecting a nurse station to a patient station via telephone, is more economical than a home visit, thereby providing both convenience and cost savings.

SUMMARY OF THE INVENTION

Video conferencing used for medical visits in the prior art did little more than substitute for a medical visit and provide telemetry of vital signs. The patient station of the present invention provides novel features which extend the functions of video conference equipment to provide functions not available with traditional medical teleconferencing equipment.

Through a five button keypad, the patient has access to a windowed system of instructions and information concerning medications, procedures, or visitations (both electronic and personal), that were placed there by the nurse, either initially or downloaded on line. The instructional video, audio and text is used by the patient and nurse on line, to explain medical procedures during an electronic visit, or to review as necessary afterwards. The customized audio, video and text information transforms the patient station into a highly personalized information source which can be reviewed by the patient when the unit is off line. Thus, when the patient needs to review a procedure again, such as the steps for changing a sterile bandage, the patient can do so at any time at their convenience, at home.

A five button keypad achieves all of the complex functions described herein by the use of notations on the video screen which define and redefine the functions of the keypad buttons. For this purpose, the buttons are disposed adjacent to the video screen whereby the function of each button is defined by the notation appearing on the video screen adjacent to each respective button. In such manner, intuitive ease of operation is provided to the patient.

Patients want information about their illness, and often need reinforcement regarding their own care. In this sense, the patient station of the present invention becomes a personal medical assistant, containing all of the background medical information, the advice of the doctor, and the special instructions which pertain to the particular medical condition of the patient. To provide custom programming of the patient station, the nurse selects appropriate information from a library of audio, video and text material, and enters customized instructions from the doctor's prescriptions, all of which is then downloaded into the patient station.

Customized menu information may be implemented by a linked list data structure. Data screens are represented by a display record containing choices for the patient to make. Each choice in the display record contains pointers (links) to either an operation or to another display record. An operation can for example, be an instruction such as a canned video clip. The linked list of display records and operations form a system of menu choices and information through which the patient can navigate to find just the advise and information required.

In such manner, the patient station is programmed to become a personal medical assistant, containing customized knowledge for each particular patient.

Medical procedures and medications must often be administered to the patient on a schedule. In many cases, the schedules are complex and a patient may forget a scheduled event. For example, one medication may need to be taken once a day, an hour before a meal, while an other may need be taken three times a day after a meal. Procedures are also scheduled. For example, a surgically installed intravenous tube may need to be flushed once a day, while the site of chest entry of the tube may need a sterile dressing change once a week.

The patient station of the present invention is programmed by the nurse to remind the patient of all scheduled events, including visitations. An alarm sounds at the time of the scheduled event. If not answered, the alarm is rescheduled and becomes more insistent. When the alarm is answered, audio, video or text reminders are presented to the patient. At the same time, information regarding procedures is available to the patient at the touch of a button. Afterwards, the patient confirms that the medication has been taken or the procedure has been performed. A record of compliance is stored in the patient station, which record is uploaded to the nurse station and compared to the original event schedule. Discrepancies can be followed up by the nurse at the next visitation.

A schedule of events (both medication and procedural) may be implemented in a table form. Each entry in the table contains an action entry and a corresponding time entry. In operation, the table is scanned by a real time operating system which scans the table, comparing the time entries to a real time clock. When real time equals or exceed a table time entry, the corresponding action entered in the table is undertaken. After the action is taken or acknowledged, the entry is marked so that actions will not be unintentionally duplicated.

In such manner, off line as well as on line, the patient station of the present invention is an intelligent personal medical assistant, programmed by the nurse to provide customized reminders and information necessary for the efficient management of the patient's illness in accordance with the prescriptions and directions of the doctor.

The patient station is easy to use. Only five large buttons are needed to operate the patient station. Additionally, the video camera at the patient station is remotely controlled by the nurse in order to view the patient. The patient assumes a position in front of the patient station which is convenient to the patient. The nurse then adjusts the video camera to capture an image to make accurate observations. It is more convenient and desirable for the patient that the remote video camera move rather than the patient move. For this purpose, the nurse station in the present system remotely controls the pan, tilt and zoom of the camera at the patient station.

DETAILED DESCRIPTION

Figure 1:
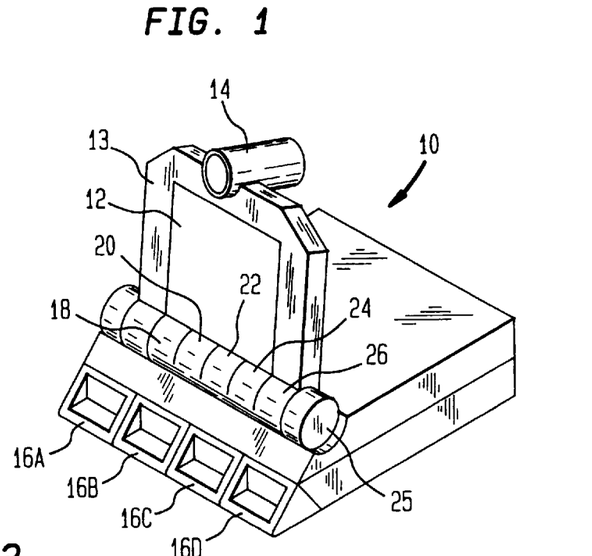
FIG. 1 is an isometric view of a patient station in accordance with the present invention.

A perspective view of the patient terminal 10 with video screen 12 and video camera 14 for the home health care system of the present invention is shown in FIG. 1. There are four drawers 16A, 16B, 16C and 16D. Each drawer is used for a particular purpose such as to hold a sensor (e.g., thermometer, blood pressure and temperature cuff, stethoscope) or medication. Other types of sensors include a weight scale, EKG, ECG, pulse oximeter, glucometer, and EEG.

Medical sensors are housed in separate drawers which form protective compartments to keep the sensors free of dust and other contaminants. Sensor wires or tubes are positioned to exit at back of the sensor drawer, so that when the sensor drawer is closed, the sensor is protected and an orderly appearance is maintained.

Figure 2:
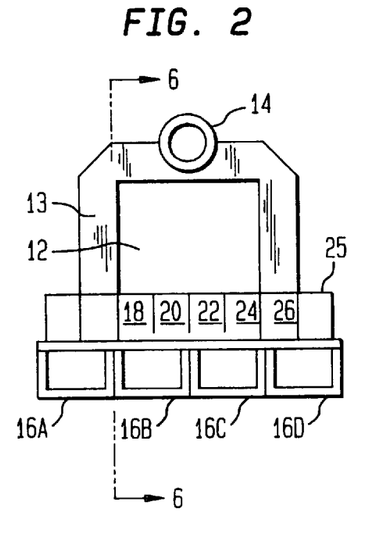
FIG. 2 is a front view of a patient station in accordance with the present invention.
Figure 3:
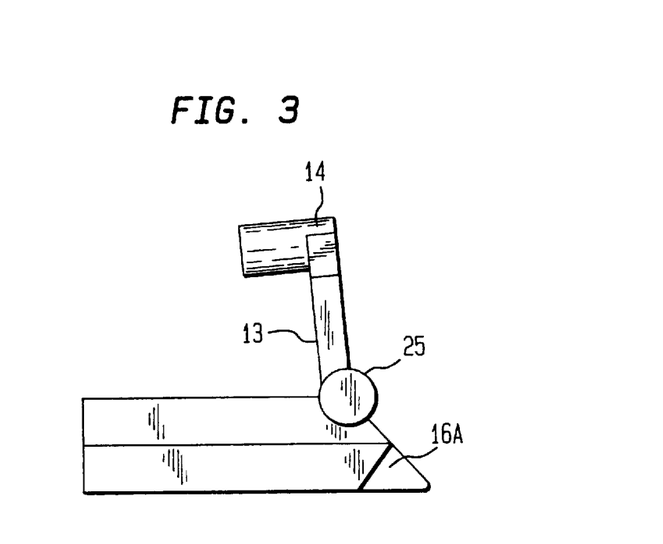
FIG. 3 is a side view of a patient station in accordance with the present invention.
Figure 4:
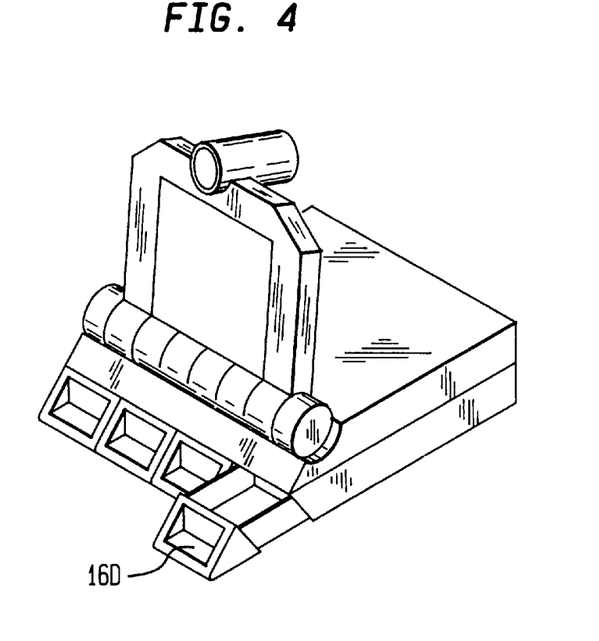
FIG. 4 is an isometric view of a patient station illustrating the operation of drawers for sensor and medication storage for use with the present invention.

The patient terminal also has five button switches 18, 20, 22, 24 and 26, used for patient input. Four of the buttons 18, 20, 22, 24 are re-definable by notation appearing on the lower portion of the video screen 12. The fifth button 26 is dedicated as a help button to provide "how to" instructions for the patient. Video screen 12 and its housing 13 rotate about shaft 25 to position both the video screen 12 and the camera 14 for proper view. Front and side views are shown in FIGS. 2 and 3 respectively. An open drawer 16D is shown in FIG. 4.

Figure 5:
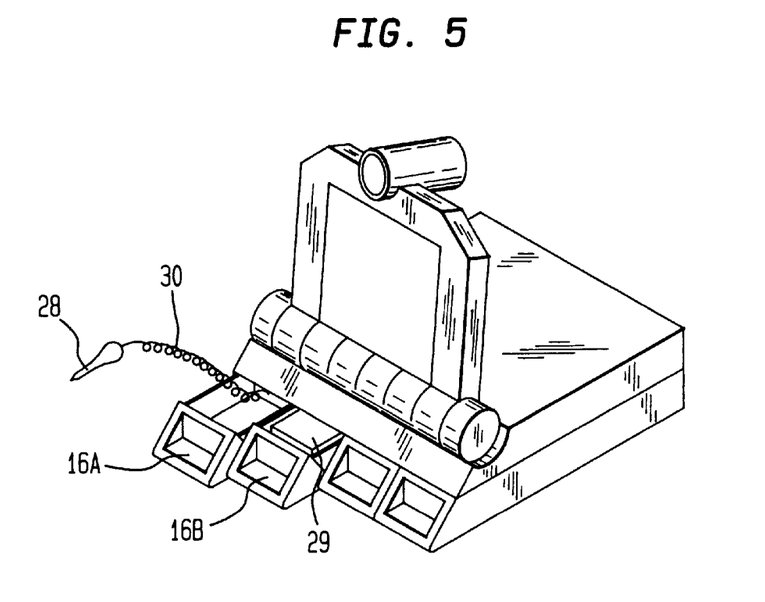
FIG. 5 is an isometric view of a patient station illustrating the operation of drawers for temperature and blood pressure sensor storage for use with the present invention.

The sensor protection aspect of the present mechanical arrangement is shown in FIG. 5. A thermometer 28 is retrieved by opening drawer 16A and removing thermometer 28 which is attached by extensible coiled cord 30. Extensible coiled cord 30 is connected to the patient station through the rear of drawer 16A so that when the thermometer is replaced in drawer 16A there are no dangling wires, and the sensor itself is kept clean.

A pressure cuff 29 is similarly kept in drawer 16B. Typically, drawer 16C is used for the stethoscope and the last drawer 16D is typically used to hold medications (which may have sub-compartments to hold separate doses). Other standard sensors as required may be included, or special sensors customized for a specific patient's condition.

Figure 6:
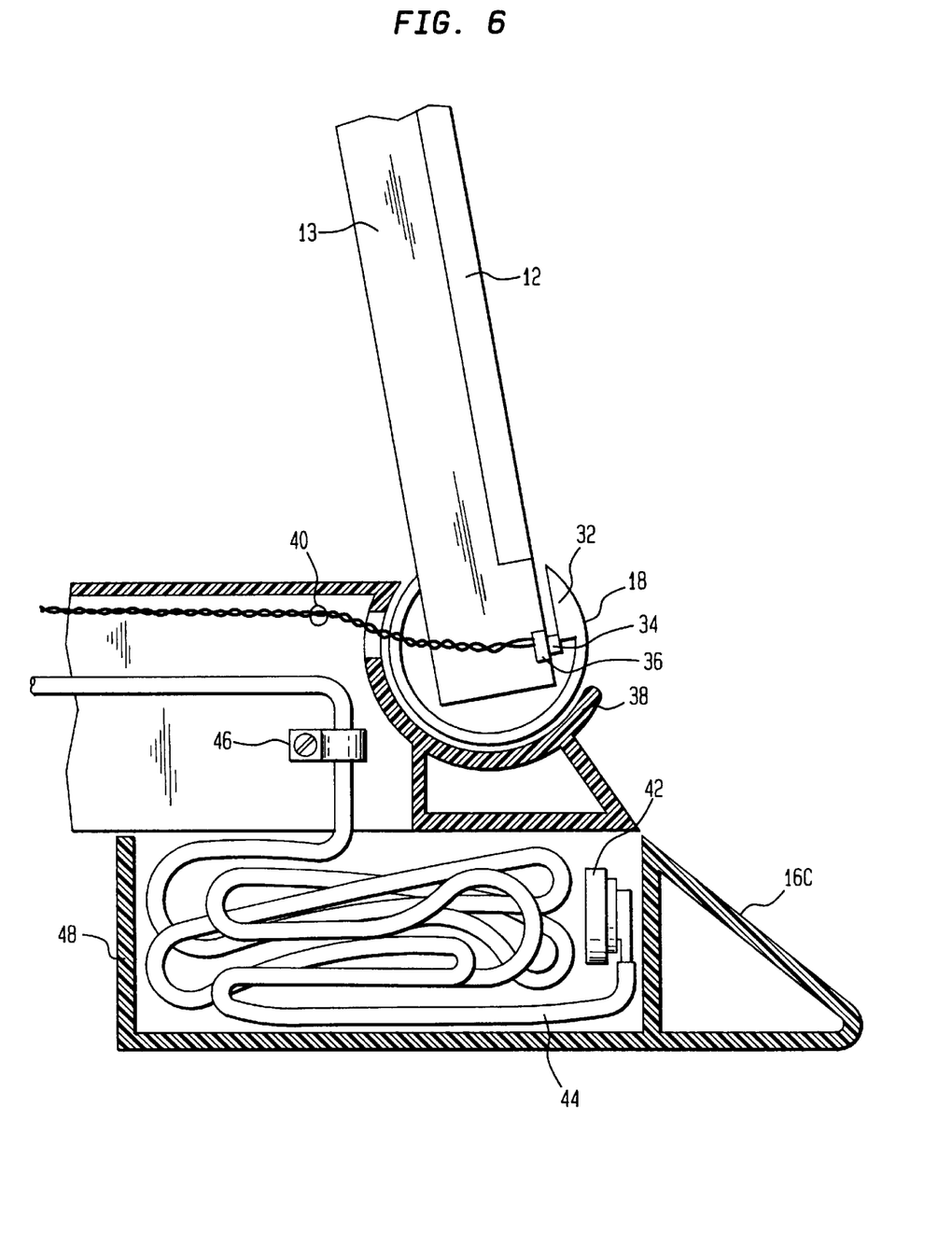
FIG. 6 is a cross sectional view of a patient station illustrating the operation of a sensor drawer for storage of a stethoscope sensor, and the operation of a patient keypad button in accordance with the present invention.

A cross-sectional view of the patient terminal is shown in FIG. 6. The drawer 16C holds an electronic stethoscope sensor 42 and cord 44 through a strain relief 46. The rear panel 48 retains the stethoscope 42, 44 in drawer 16C. Cord 44 exits through the open top of the drawer 16C, but alteratively may exit through the rear panel 48 or bottom or side panels. A representative switch arrangement for switch 18 is also shown in FIG. 6 (and in somewhat larger detail in FIG. 7). An electrical switch 36 mounted on housing 13 has a push button 34. The switch panel 18 is a semi-circular member having a protrusion 32 disposed adjacent to button 34 of switch 36. The semi-circular member 18 rests in a support 38. When the semi-circular member 18 is deflected by finger pressure, protrusion 32 contacts button 34, thereby effecting a contact closure within switch 36. Wires 40 communicate the switch closure to the central controller in the patient station.

Figure 7:
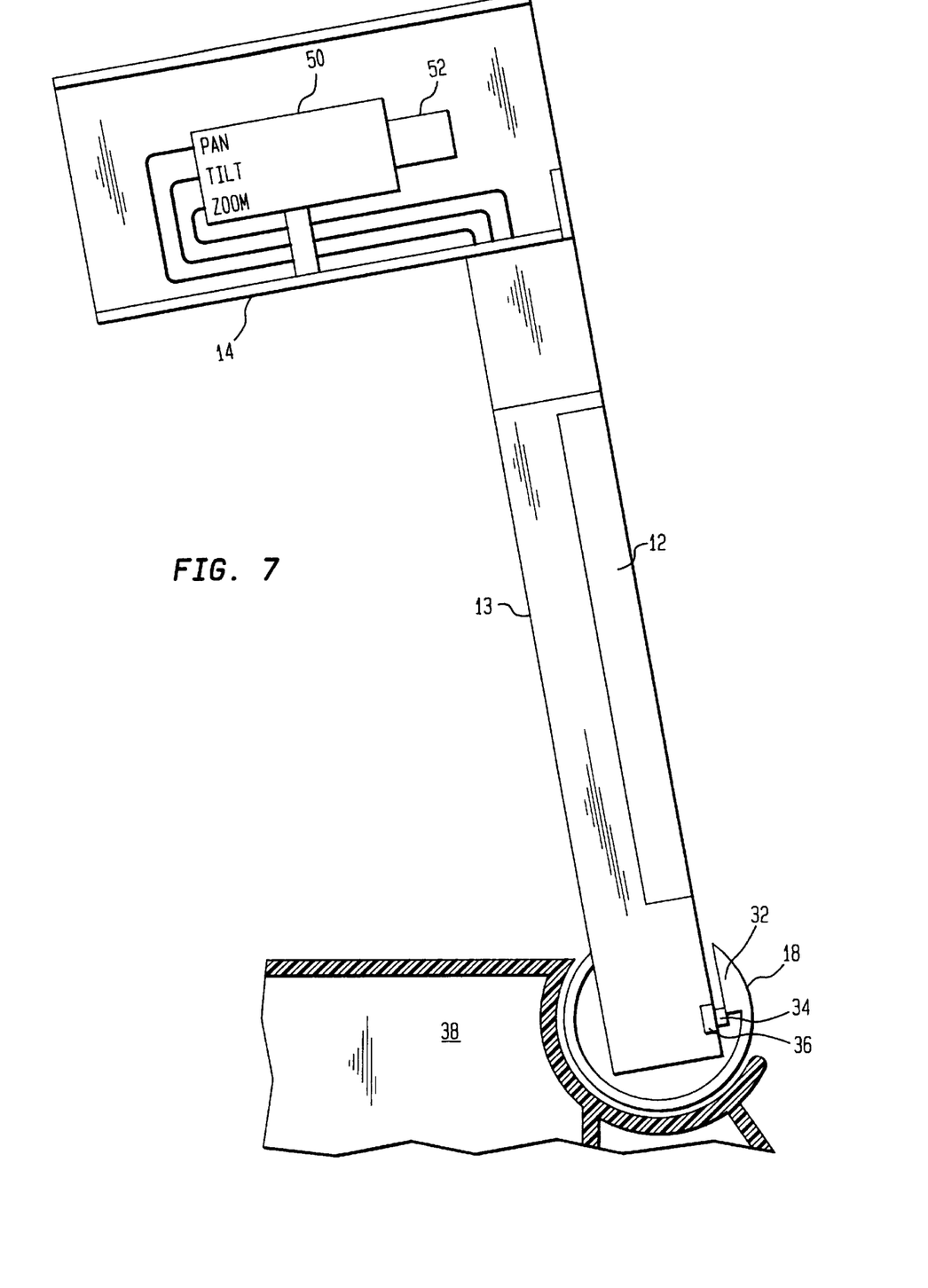
FIG. 7 is a cross sectional view of a patient station illustrating the operation of a remotely controlled video camera, and the operation of a patient keypad button in accordance with the present invention.
Figure 9:
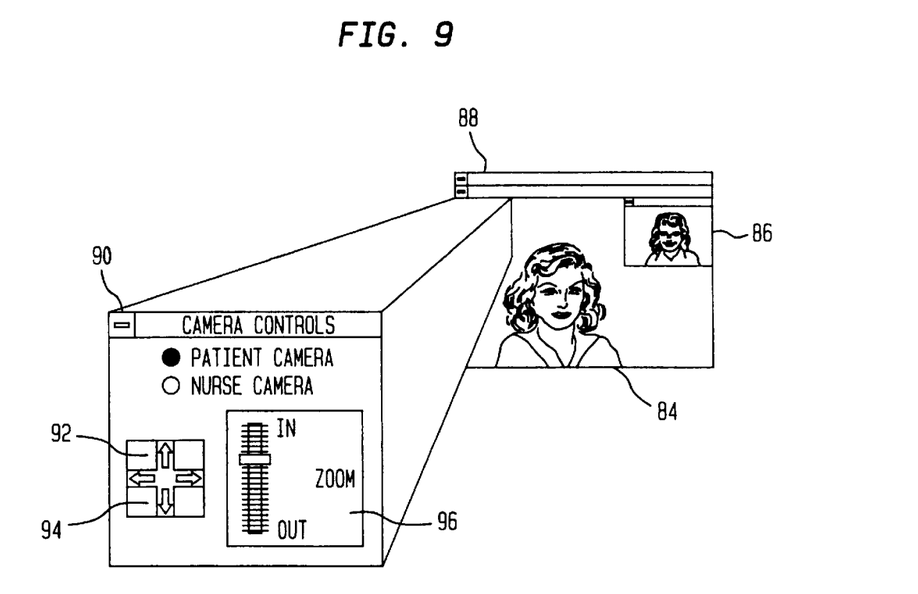
FIG. 9 is a detail of the video screen view at the nurse station, illustrating video camera controls for pan, tilt and zoom in accordance with the present invention.

A detail of the camera 14 is shown in FIG. 7 in which pan, tilt and zoom controls the position of camera 50 and lens 52. The patient station video camera articulation is controlled from the nurse station video screen. In FIG. 9, the on-screen camera controls 90 for pan 92, tilt 94 and zoom 96 are shown. The split screen 88 displays the patient in the main portion 84 of the screen and also displays the nurse's own image in the corner 86 as it appears to the patient.

Figure 8:
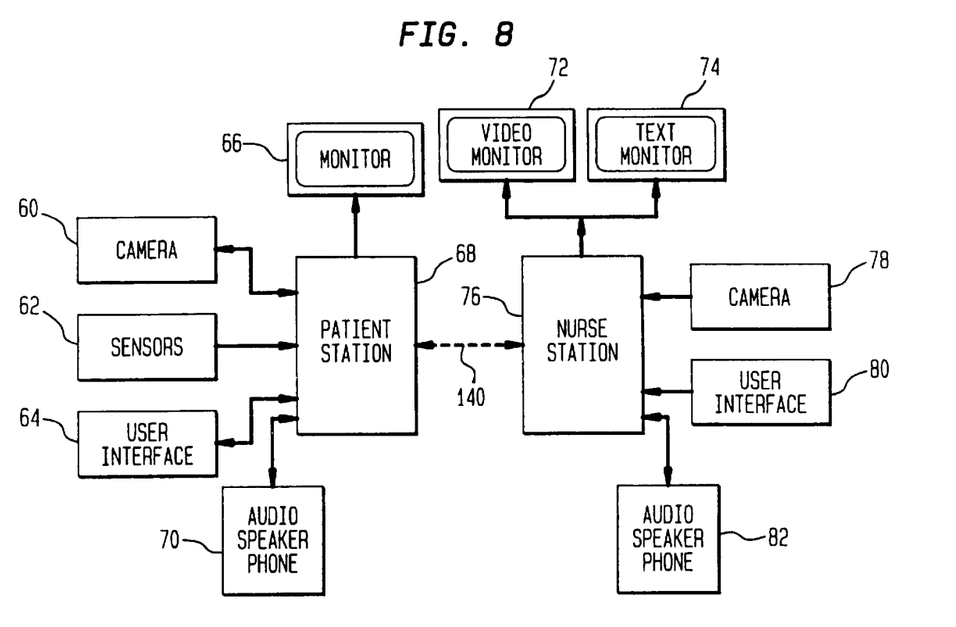
FIG. 8 is a block diagram of a system including a nurse station and a patient station coupled by a telephone line in accordance with the present invention.

An overall system structure is shown in FIG. 8. The nurse station 76 includes a camera 78, user interface 80, audio speaker phone 82 and two monitors 72, 74. One monitor 72 is used for video images of the patient, while the second monitor 74 is used for text.

The patient station 68 includes a camera 60, sensors 62, user interface 64, audio speaker phone 70, and a video monitor. A plain telephone line connects the nurse station to the patient station.

Figure 11:
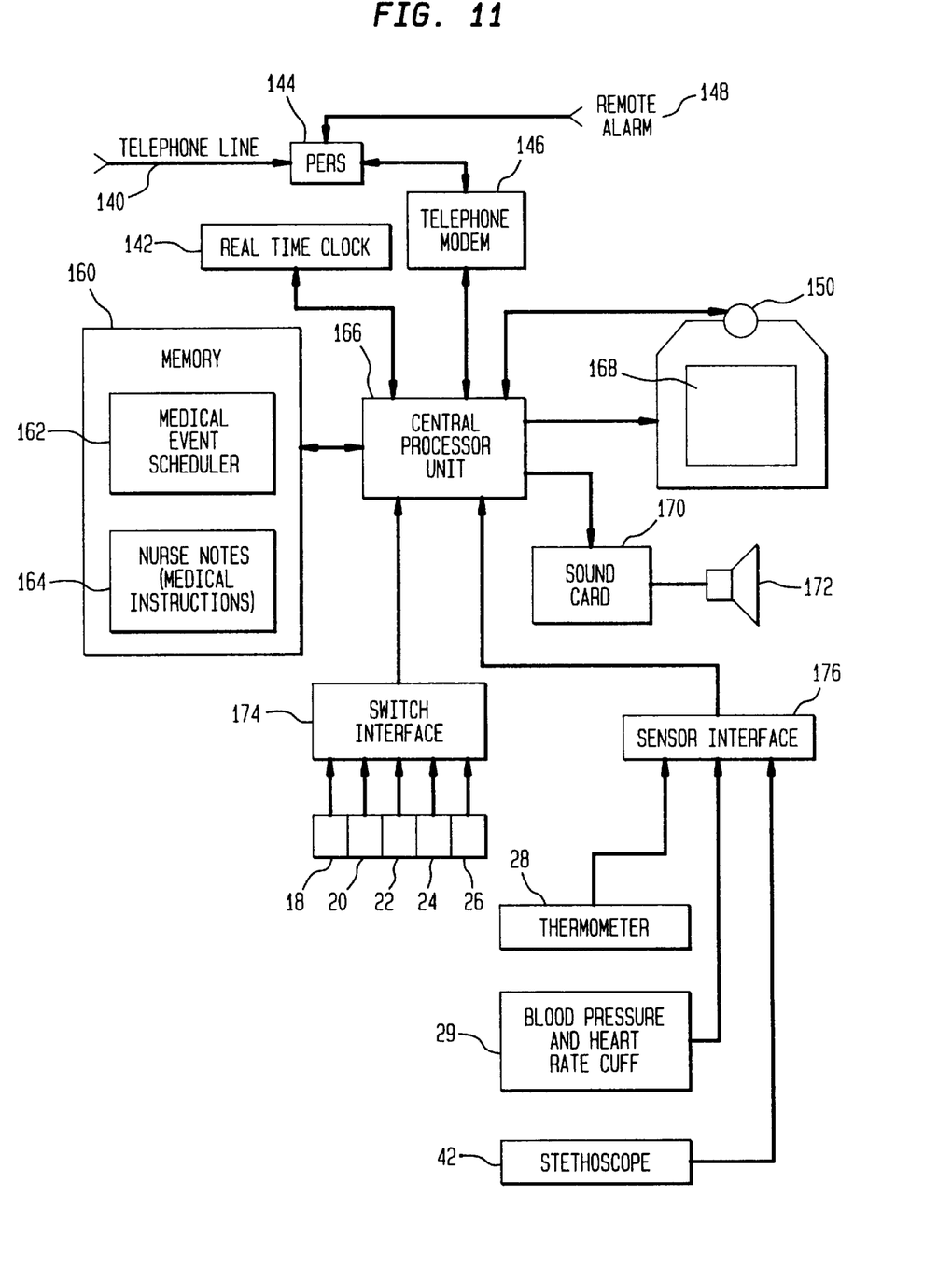
FIG. 11 is a block diagram of a patient station in accordance with the present invention.

A block diagram of the patient station is shown in further detail in FIG. 11. A central processor unit 166 is coupled to a memory 160, a real time clock 142, modem 146, video camera 150, video screen 168, sound card 170 and speaker 172. Additionally, the sensors for temperature 28, blood pressure and pulse rate 29, and a stethoscope 42 are coupled to the central processor 166 through a sensor interface 176. Similarly, the switch inputs 18, 20, 22, 24, and 26 are coupled to the central processor 166 through a switch interface 174. The telephone line 140 is coupled to the modem 146 through a personal emergency response system (PERS) 144. The personal emergency response system 144 responsive to a remote alarm 148, to dial an emergency number on telephone line 140 to summon help.

In operation, the nurse station is connected to the patient station via a regular telephone. In an electronic visitation, by video conference or teleconference, the nurse and patient see and hear each other. Additionally, the nurse station transmits data to be downloaded into the patient station. The transmitted data is selected by the nurse from a library of material in accordance with the doctor's instructions and prescriptions, thus being customized to the needs of the particular patient. In particular, schedules of medical events (medications, procedures and the like) are transmitted as medical event schedules by the nurse station to the patient station. Additionally, the nurse station transmits medical information (nurse notes as text, audio, video and/or data) to the patient station for storage.

At the patient station, the medical event scheduler 162 and the nurse notes 164 are held in memory 160. The contents of the medical event scheduler 162 and the nurse notes 164 may either be installed in the patient station at the patient's home through an internal floppy disk reader (not shown) coupled to the central processor 166, or later downloaded to the patient station from the nurse station at any time after installation of the patient station. The patient accesses the medical schedule and nurse notes via the five button 18, 20, 22, 24, 26, keyboard.

Figure 10:
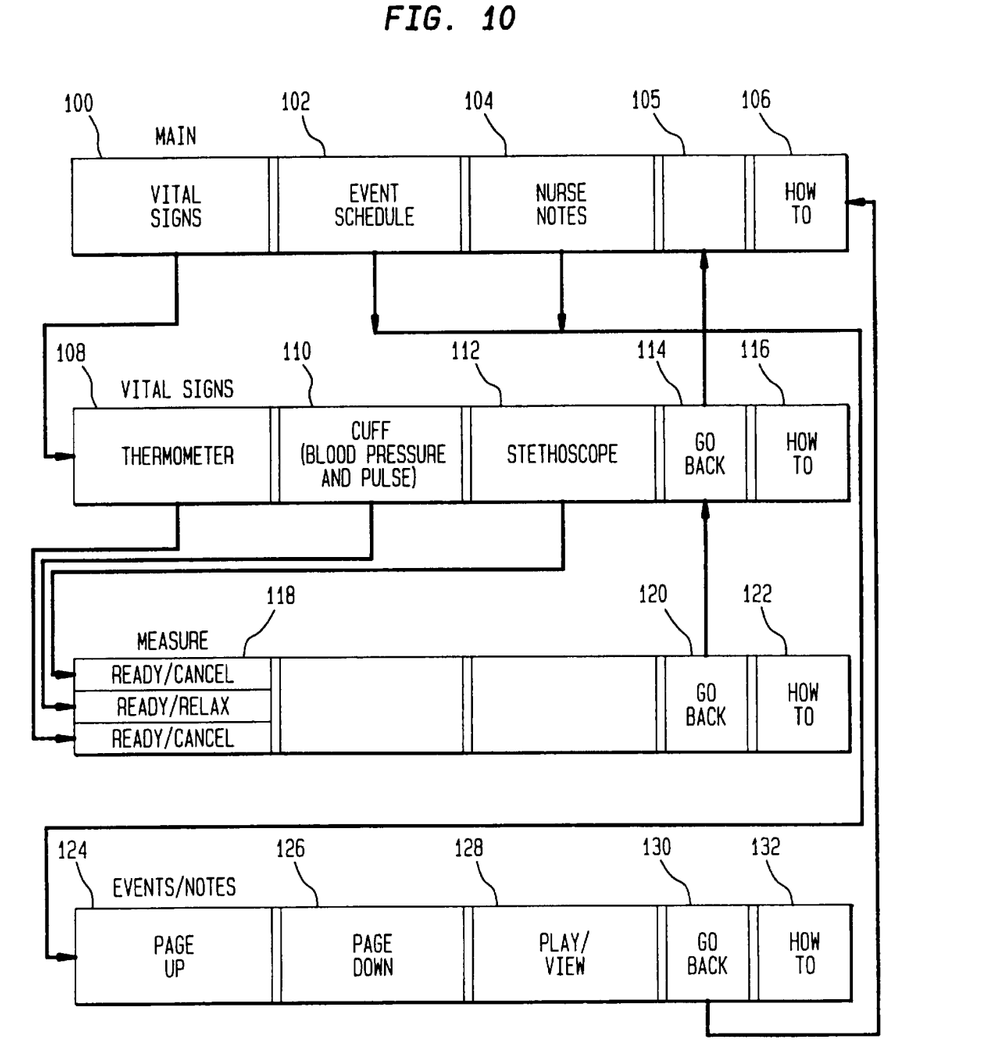
FIG. 10 is a flow chart of the definition and redefinition of the five button switches 18, 20, 22, 24 and 26 shown in FIG. 1, in accordance with the present invention.

The definition and redefinition of the five buttons switches 18, 20, 22, 24 and 26 is shown in the flow chart of FIG. 10. Each row of five horizontal boxes in FIG. 10 represents the five buttons. The content of each box represents the redefinition of each switch. The right most button is always the "how to" button, or the help button.

Initially, the main button menu on the video screen (reference 12 in FIG. 1) is displayed. The patient may choose to take vital signs 100, view the scheduled events 102, receive nurse notes 104 (medical instructions), or find out how and when 106 to operate the first four buttons. Button 105 not being used, is shown in blank.

If vital signs 100 is chosen from the button menu, then the vital signs button menu is displayed. From there, the patient can choose to operate a thermometer 108, a pressure and pulse cuff 110, a stethoscope 112, or to go back 114 (return) to the previous button menu.

After choosing a sensor, the measure menu comes up. First, the patient chooses the "ready" 118 button after positioning the sensor, which is followed by either "cancel" (for the thermometer or stethoscope) or relax (for the cuff), for the same button 118 depending on which sensor was chosen. After the measurement, the "go back" button 120 returns the patient to the vital signs menu, and thereafter the "go back" button 114 returns the patient from the vital signs menu to the main menu.

If event schedule 102 or nurse notes 104 is chosen from the main button menu, then the buttons are redefined in the event/notes menu to be "page up" 124, "page down" 126 and "play/view" 128. The "how to" button 132 provides instructions on how to use the buttons. Page up or page down step through the medical information selected for downloading by the nurse. Play/view actives the patient station to show video and/or audio clips illustrating how to use an indicated medication or perform a medical procedure. When finished, the patient returns to the main menu by the "go back" button 130.

Figure 12:
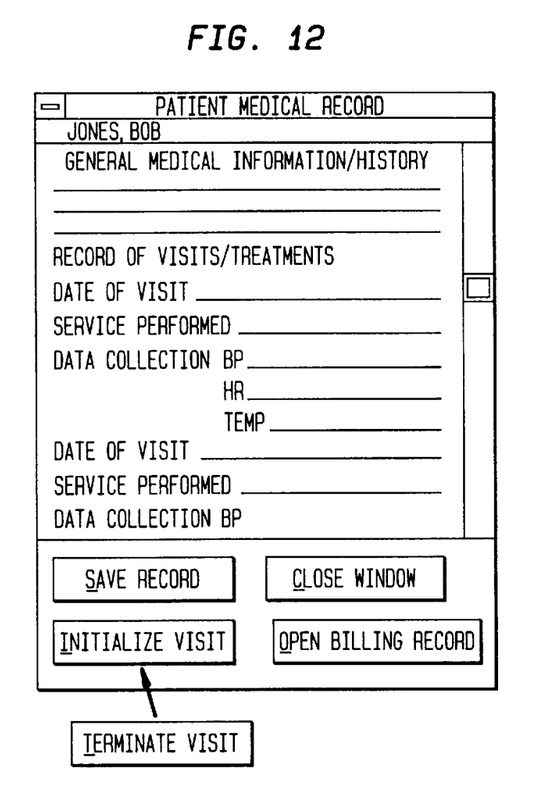
FIGS. 12 and 13 show typical patient information window details as appearing on the nurse station data screen.
Figure 13:
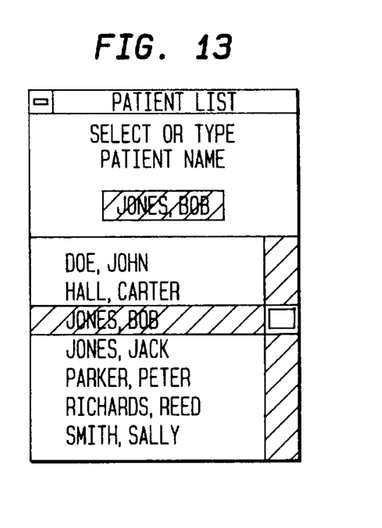
Figure 15:
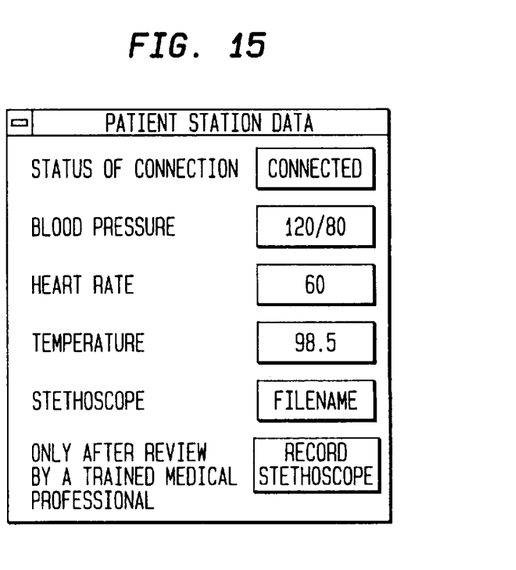
FIG. 15 shows a typical patient station vital signs information as appearing on the nurse station data screen.

The nurse station includes menu choices so that the nurse can contact and program the patient station. Starting from a patient list in FIG. 13, a patient record as in FIG. 12 is retrieved. The nurse can initiate a teleconference visit with the patient by clicking on the "initiate visit" screen button. During the video conference, the screen button becomes "terminate visit." Privacy measures are provided to assure that the patient consents to accept the conference call before video is activated. During the teleconference, acquired vital signs data are displayed in a window such as shown in FIG. 15, and records of medical compliance are uploaded from the patient station to the nurse station. The nurse can also initiate a call, without a video conference visit, in order to download a new medical event schedule or new nurse notes.

Figure 16:
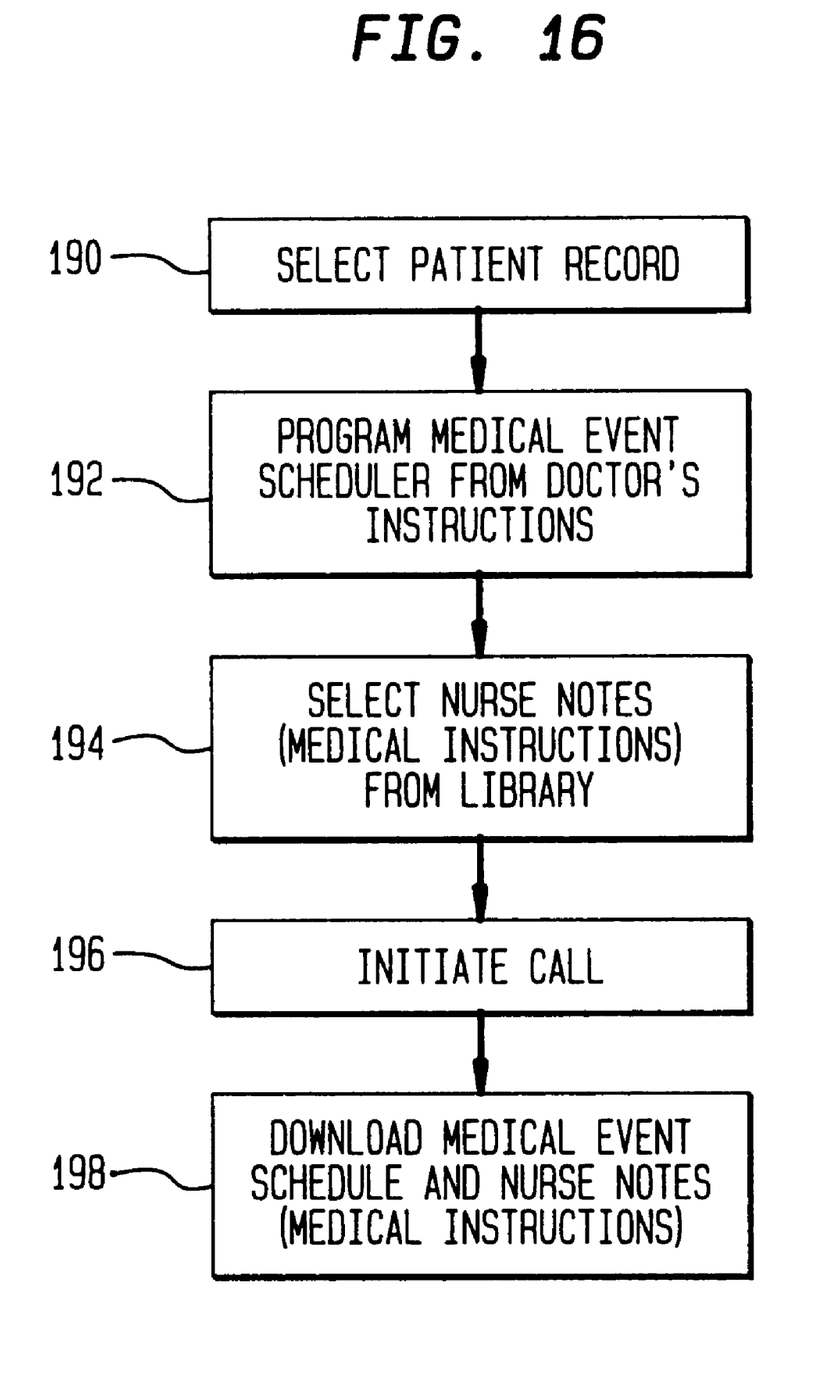
FIG. 16 is a flow chart diagram illustrating the sequence of programming steps for programming the patient station to contain customized medical information, and customized schedules for medication and medical procedures for each particular patient.

The process for programming the patient station with customized medical schedules and instructions is shown in FIG. 16. The patient record is selected at step 190 and displayed to the nurse. The medical event scheduler is programmed at step 192 by the nurse from the doctor's instructions. For example, if medication is to be taken twice a day with food, the nurse selects appropriate canned instructions for the medication or writes special instructions according to the doctor's prescription.

Similarly, medical instructions appropriate to the patient's condition are selected from a library of instructions at step 194, or special instructions provided by the doctor. The nurse then initiates at step 196 a call (with or without a visitation), and the event schedules and nurse notes (medical instructions) are subsequently downloaded at step 198 to the patient station.

As indicated, medical instructions are available to the patient by operation of the five button: switches 18, 20, 22, 24 and 26 shown in FIG. 1. A medical event schedule is a list of days, dates and times in which a medical event is due. To execute the medical event schedule 162 (from FIG. 11) the real time clock 142 is compared to the designated time in the medical event schedule. If real time is at or later than a scheduled medical event, an alarm is set. When the medical event is acknowledged by the patient, the alarm is turned off.

Figure 14:
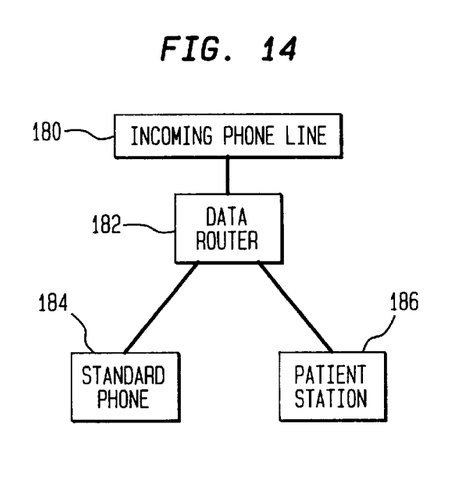
FIG. 14 shows a data router for discriminating incoming telephone calls intended for the telephone, as compared to incoming calls intended for the patient station.

As shown in FIG. 14, the patient station 186 discriminates between incoming calls 180 on the phone line intended for the telephone 184 from incoming calls intended for the patient station 186. The incoming call is routed in data router 182, which forwards the incoming call to the appropriate destination.

Medical event schedules and nurse notes (medical information) are highly customized to the patient. For example, a nurse note for a diabetic patient may consist of a video and audio instruction how to fill a syringe and administer a dose of insulin. For a burn victim, a nurse note on how to change a dressing is appropriate. Similarly, a medical event for a diabetic may be an alarm to take a dose of insulin, while for a burn victim, the scheduled event is a dressing change. In such manner, the patient terminal is a personal medical assistant, educating the patient. At the same time, the patient terminal is a watchful attendant reminding the patient when to take or apply medication, record vital signs, or visit with the nurse by teleconference.

What is claimed is:

1. A method of use of a medical teleconference system including a nurse station having a plurality of sets of instructions pertaining to treatment of patients and a patient station having a definable-function five button keypad, a video monitor, a video camera, and an audio speaker phone, said system having a communications link connecting said nurse station and said patient station, said method comprising:

activating said patient station and said nurse station;

selecting at said nurse station a set of instructions relating to medical treatment of a patient that define specific functions for said five buttons of said patient station;

transmitting said set of instructions from said nurse station to said patient station;

storing said set of instructions at said patient station; and recalling said set of instructions so as to display said set of instructions adjacent to said five buttons of said patient station, so that said instructions can be reviewed by said patient at said patient station.

2. A method in accordance with claim 1, further comprising:

disconnecting said communication link between said nurse station and said patient station after transmitting said instructions.

3. A method in accordance with claim 1, wherein said set of instructions are text instructions displayed on said video monitor.

4. A method in accordance with claim 1, wherein said set of instructions are audio instructions presented through said speaker phone.

5. A method in accordance with claim 1, wherein said set of instructions comprises a video displayed on said video monitor.

6. A medical teleconference apparatus comprising:

a nurse station having a plurality of sets of instructions pertaining to treatment of patients;

a patient station having a definable-function five button keypad, a video monitor, a video camera, and an audio speaker phone;

a communications link connecting said nurse station and said patient station means for selecting at said nurse station a set of instructions relating to medical treatment of a patient that define specific functions for said five buttons of said patient station;

a transmitter for transmitting said set of instructions from said nurse station to said patient station;

a memory for storing said set of instructions at said patient station; and means for recalling and displaying said set of instructions so as to display said set of instructions adjacent to said five buttons of said patient station, so that said instructions can be reviewed by said patient at said patient station.

7. An apparatus in accordance with claim 6, further comprising:

means for disconnecting said communication link between said nurse station and said patient station after transmitting said instructions.

8. An apparatus in accordance with claim 6, wherein said set of instructions are text instructions displayed on said video monitor.

9. An apparatus in accordance with claim 6, wherein said set of instructions are audio instructions presented through said speaker phone.

10. An apparatus in accordance with claim 6, wherein said set of instructions comprises a video displayed on said video monitor.

* * * * *